(12) United States Patent
Peng et al.

(10) Patent No.: US 10,408,679 B2
(45) Date of Patent: Sep. 10, 2019

(54) TERAHERTZ TIME-DOMAIN SPECTROSCOPY SYSTEM

(71) Applicants: SHENZHEN TERAHERTZ SYSTEM EQUIPMENT CO., LTD., Shenzhen (CN); SHENZHEN INSTITUTE OF TERAHERTZ TECHNOLOGY AND INNOVATION CO., LTD., Shenzhen (CN)

(72) Inventors: Shichang Peng, Shenzhen (CN); Yi Pan, Shenzhen (CN); Chen Li, Shenzhen (CN); Qing Ding, Shenzhen (CN)

(73) Assignees: Shenzhen Institute of Terahertz Technology and Innovation, Shenzhen, Guangdong Province (CN); Shenzhen Terahertz System Equipment Co., LTD., Shenzhen, Guangdong Province (CN)

( * ) Notice: Subject to any disclaimer, the term of this patent is extended or adjusted under 35 U.S.C. 154(b) by 0 days.

(21) Appl. No.: 15/561,005

(22) PCT Filed: Aug. 4, 2016

(86) PCT No.: PCT/CN2016/093264
§ 371 (c)(1),
(2) Date: Sep. 22, 2017

(87) PCT Pub. No.: WO2017/197776
PCT Pub. Date: Nov. 23, 2017

(65) Prior Publication Data
US 2018/0306644 A1    Oct. 25, 2018

(30) Foreign Application Priority Data

May 19, 2016  (CN) .......................... 2016 1 0338618

(51) Int. Cl.
*G01J 5/02*      (2006.01)
*G01J 3/433*     (2006.01)
(Continued)

(52) U.S. Cl.
CPC .......... *G01J 3/4338* (2013.01); *G01J 3/0205* (2013.01); *G01J 3/0224* (2013.01); *G01J 3/2803* (2013.01);
(Continued)

(58) Field of Classification Search
CPC ...... G01J 3/0205; G01J 3/4338; G01J 3/0224; G01J 3/2803; G01J 3/42; G01J 2003/2806;
(Continued)

(56) References Cited

U.S. PATENT DOCUMENTS 6,320,191 B1    11/2001   Rudd
2002/0118371 A1  8/2002   Jiang et al.
(Continued)

FOREIGN PATENT DOCUMENTS

CN    2874476       2/2007
CN    101701852     5/2010
(Continued)

OTHER PUBLICATIONS

Chen et al., "Electro-otpic transceivers for terahertz-wave applications," 2001, Journal of Optical Society of America, vol. 18, No. 6, pp. 823-831. (Year: 2001).*
(Continued)

*Primary Examiner* — Kiho Kim
(74) *Attorney, Agent, or Firm* — Jason P. Mueller; Adams and Reese LLP

(57) ABSTRACT

The present application relates to a terahertz time-domain spectroscopy system. In this terahertz time-domain spectroscopy system, the femtosecond laser light radiated by the
(Continued)

femtosecond laser is collimated by a first diaphragm, and then is split by a beam splitter into a pump light and a probe light. The pump light passes through the first light path module to generate a terahertz pulse, and the probe light passes through the first light path module to generate a linear polarization probe light having the same optical distance as that of the pump light. The linear polarization probe light and the terahertz pulse are combined by a beam combiner to obtain a light beam to be detected carrying the terahertz pulse information. Two electro-optical crystals with the same thickness are used in a detection device simultaneously. Changing the crystal axis angle of the two electro-optical crystals, there is a phase compensation to the two components o light and e light of the probe light, so as to realize linear detection to high power terahertz pulse and improve measurement accuracy.

10 Claims, 1 Drawing Sheet

(51) Int. Cl.

| | | |
|---|---|---|
| *G01N 21/3581* | (2014.01) | |
| *G01N 21/49* | (2006.01) | |
| *G01N 21/3563* | (2014.01) | |
| *G01N 21/3577* | (2014.01) | |
| *G01J 3/42* | (2006.01) | |
| *G01J 3/28* | (2006.01) | |
| *G01N 21/3586* | (2014.01) | |
| *G01J 3/02* | (2006.01) | |

(52) U.S. Cl.
CPC ............ *G01J 3/42* (2013.01); *G01N 21/3563* (2013.01); *G01N 21/3577* (2013.01); *G01N 21/3581* (2013.01); *G01N 21/3586* (2013.01); *G01N 21/49* (2013.01); *G01J 2003/2806* (2013.01); *G01J 2003/421* (2013.01); *G01J 2003/423* (2013.01); *G01J 2003/425* (2013.01); *G01N 2201/06113* (2013.01)

(58) Field of Classification Search
CPC ........... G01J 2003/421; G01J 2003/423; G01J 2003/425; G01N 21/3586; G01N 2201/06113; G01N 21/3581; G01N 21/49; G01N 21/3563; G01N 21/3577
See application file for complete search history.

(56) References Cited

U.S. PATENT DOCUMENTS

| | | | |
|---|---|---|---|
| 2005/0100866 A1* | 5/2005 | Arnone | ............... A61B 5/0088 433/215 |
| 2011/0013265 A1 | 1/2011 | Nishimura | |
| 2018/0031469 A1* | 2/2018 | Aiko | ................. G01N 21/3581 |

FOREIGN PATENT DOCUMENTS

| | | |
|---|---|---|
| CN | 101813619 | 8/2010 |
| CN | 101918889 | 12/2010 |
| CN | 201662531 | 12/2010 |
| CN | 203606417 | 5/2014 |
| CN | 205785527 | 12/2016 |

OTHER PUBLICATIONS

Gu, Chunming et al. "Effects of probe-beam polarization direction on THz detection in ZnTe", Journal Infrared Millimeter and Waves, vol. 23, No. 5, Oct. 31, 2004, pp. 333-336.

Turchinovich, Dmitry et al. "Performance of combined <100> - <110> ZnTe crystals in an amplified THz time-domain spectrometer", Optics Communications, vol. 270, No. 1, Feb. 28, 2007, pp. 96-99.

* cited by examiner

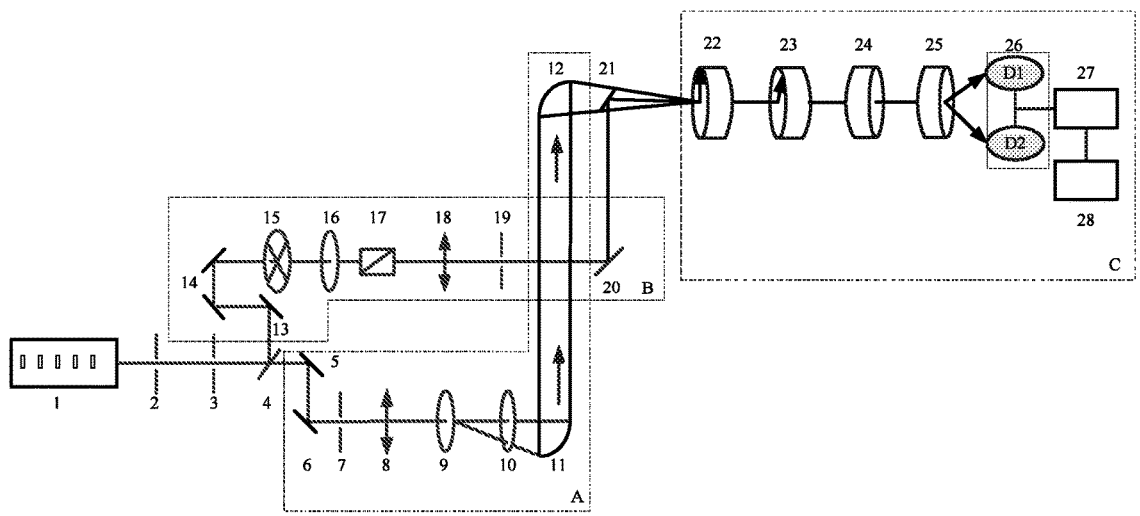

TERAHERTZ TIME-DOMAIN SPECTROSCOPY SYSTEM

TECHNICAL FIELD

Aspects of the present disclosure relate to the terahertz technical field, and more particularly, to a terahertz time-domain spectroscopy system.

BACKGROUND

The frequency band of Terahertz (THz, THz=$10^{12}$ Hz) refers to an electromagnetic radiation range with a frequency from 0.1 THz to 10 THz and a wavelength between microwave and infrared light. Terahertz radiation can provide the capability of ultrafast time resolved spectroscopy because of its short time scale. Terahertz radiation can be used to penetrate through some materials, such as organisms, dielectric medium, and gas phase material. Material's composition, physical state, chemical state, and biological state information can be obtained by analyzing sample materials' transflective terahertz signals. Besides, terahertz radiation will not damage the tested materials because of its broad frequency band and low photon energy, so that the terahertz technology can be used in many fields, such as imaging, spectroscopic analysis, nondestructive testing, and high-speed wireless communication.

Photoconductive sampling and electro-optical sampling are two commonly used terahertz testing technologies, wherein the electro-optical sampling needs low pulse energy and has high sensitivity and a broad probe bandwidth. However, this technology has some defects. The electro-optical sampling is based on electro-optical effect. Terahertz pulse will change the birefringence electro-optical crystal's refractive index when penetrating through the crystal, which causes probe light's polarization state to change. After modulating light path, the illumination difference of two components of the probe light is detected to calculate the intensity of the terahertz pulse. However, this method can only be applied to terahertz signal with low intensity. Applying this method to terahertz signal with high intensity will cause signal distortion, which results in wrong information.

SUMMARY

With respect to the above problem, it is necessary to propose a terahertz time-domain spectroscopy system with simple structure and high measurement accuracy of terahertz pulse signal.

A terahertz time-domain spectroscopy system comprises a femtosecond laser, a first diaphragm, and a beam splitter; the femtosecond laser light radiated by the femtosecond laser is collimated by the first diaphragm, and then is split by the beam splitter into a pump light and a probe light; the terahertz time-domain spectroscopy system also comprises a first light path module, a second light path module, a beam combiner, and a detection device;

the pump light generates a terahertz pulse by the first light path module; the probe light generates a linear polarization probe light having the same optical distance as that of the pump light by the second light path module;
the probe light and the terahertz pulse are combined by the beam combiner to obtain a light beam to be detected carrying the terahertz pulse information;
the detection device is used to detect the light beam to be detected; in the propagation direction of the light beam to be detected, the detection device subsequently comprises a first electro-optical crystal, a second electro-optical crystal, a quarter wave plate, a Wollaston prism, a photoelectric detector, a lock-in amplifier, and an information processing device; the first electro-optical crystal and the second electro-optical crystal have the same thickness, and the crystal axis angle of the first electro-optical crystal and the second electro-optical crystal can be adjusted.

In an embodiment, both of the first electro-optical crystal and the second electro-optical crystal are sphalerite crystal.

In an embodiment, the crystal axis angle of the first electro-optical crystal and the second electro-optical crystal is 180°.

In an embodiment, the information processing device determines the amplitude of the terahertz pulse according to the following formula:

$$E_{THz} = (n^2 \gamma_{41})^{-1} \sqrt{\left(\frac{2\pi nL}{\lambda} * \frac{3}{4}\right)^{-1} * \arcsin(\Delta I/I)},$$

wherein n is the intrinsic refractive index when zinc telluride crystal is not subjected to terahertz field, $\gamma_{41}$ is the electro-optical tensor of the zinc telluride crystal, L is the thickness of the zinc telluride crystal, $\lambda$ is the central wavelength of the femtosecond laser, $\Delta I$ is the light intensity difference of o light and e light of the probe light detected by the photoelectric detector, and I is the sum of o light and e light detected by the photoelectric detector.

In an embodiment, in the propagation direction of the pump light, the first light path module subsequently comprises a plenty of reflectors, a second diaphragm, a first lens, a terahertz pulse emitting device, a first parabolic mirror, and a second parabolic mirror;
the terahertz pulse emitting device is used to radiate a terahertz pulse;
the first parabolic mirror is disposed oppositely the second parabolic mirror, and the first parabolic mirror is used to collimate the terahertz pulse; the second parabolic mirror is used to focus the terahertz pulse.

In an embodiment, the first light path module also comprises a silicon wafer for filtering stray lights, only permitting the terahertz pulse to pass through; the silicon wafer is placed between the terahertz emitting device and the first parabolic mirror.

In an embodiment, the terahertz emitting device is an active photoconductive antenna or a passive non-linear optical rectifying crystal.

In an embodiment, the passive non-linear optical rectifying crystal is barium metaborate crystal.

In an embodiment, in the propagation direction of the probe light, the second light path module subsequently comprises a delay line device, a chopper, a half wave plate, a Glan prism, a second lens, and a third diaphragm;
the chopper is used to provide modulation frequency for the lock-in amplifier; the half wave plate and the Glan prism are used to adjust the polarization of the probe light.

In an embodiment, the photoelectric detector is a differential photoelectric detector.

In the terahertz time-domain spectroscopy system, the pump light passes through the first light path module to generate a terahertz pulse, and the probe light passes through the first light path module to generate a linear polarization probe light having the same optical distance as that of the pump light. The linear polarization probe light and the terahertz pulse are combined by the beam combiner to obtain a light beam to be detected carrying the terahertz pulse information. Two electro-optical crystals with the same thickness are used in the detection device simultaneously. Changing the crystal axis angle of the two electro-optical crystals, there is a phase compensation to the two components o light and e light of the probe light, so as to realize linear detection to high power terahertz pulse and improve measurement accuracy.

BRIEF DESCRIPTION OF THE DRAWINGS

FIG. 1 illustrates a light path diagram of terahertz time-domain spectroscopy system.

Reference signs in FIG. 1 are as follows: femtosecond laser 1, first diaphragm 2, fourth diaphragm 3, beam splitter 4, silver reflector 5, 6,13, 20, second diaphragm 7, first lens 8, barium metaborate crystal 9, silicon wafer 10, first parabolic mirror 11, second parabolic mirror 12, delay line device 14, chopper 15, half wave plate 16, Glan prism 17, second lens 18, third diaphragm 19, beam combiner 21, first electro-optical crystal (zinc telluride crystal) 22, second electro-optical crystal (zinc telluride crystal) 23, quarter wave plate 24, Wollaston prism 25, differential detector 26, lock-in amplifier 27, and information processing device 28.

DETAILED DESCRIPTION

The detailed description set forth below in connection with the appended drawings is intended to facilitate understanding of this invention. Preferred embodiments are provided in the appended drawings. However, this invention can be implemented by a variety of forms and is not limited to the embodiments described herein. On the contrary, the embodiments are recited for the purpose of providing a thorough understanding of this disclosure.

Unless otherwise defined in this invention, all technology and science terminologies herein have the same meanings commonly understood by persons skilled in this field to which this invention belongs. Terminologies used in this specification of the invention are merely intended to describe specific embodiments and are not limited to this invention. The phrase "and/or" used herein comprises arbitrary and all the combinations of one or more related listed items.

FIG. 1 illustrates a structural diagram of a terahertz time-domain spectroscopy system. The system comprises a femtosecond laser 1, a first diaphragm 2, a fourth diaphragm 3, a beam splitter 4, silver reflectors 5, 6,13, 20, a second diaphragm 7, a first lens 8, a barium metaborate crystal 9, a silicon wafer 10, a first parabolic mirror 11, a second parabolic mirror 12, a delay line device 14, a chopper 15, a half wave plate 16, a Glan prism 17, a second lens 18, a third diaphragm 19, a beam combiner 21, a first electro-optical crystal (zinc telluride crystal) 22, a second electro-optical crystal (zinc telluride crystal) 23, a quarter wave plate 24, a Wollaston prism 25, a differential detector 26 (D1 and D2 are photoelectric probes), a lock-in amplifier 27, and an information processing device 28.

The work procedure is as follow. The femtosecond laser 1 is a titanium sapphire femtosecond laser, which can radiate a pulse laser light with 800 nanometer (nm) and 40 femtosecond (fs). The pulse laser light source's light path is collimated through the first diaphragm 2 and the fourth diaphragm 3, so as to ensure the stability of subsequent light path. The collimated light path next is split into two light paths by the beam splitter 4: one is pump light and the other is probe light, wherein the light path corresponding to the pump light is the first light path module A, and the light path corresponding to the probe light is the second light path module B.

In this embodiment, due to the spatial limitation, several silver reflectors 5, 6, 13 and 20 are provided in the first light path module A and the second light path module B to swerve corresponding light paths, so that the optical distance of the pump light in the first light path module A is equal to that of the probe light in the second light path module B. In other embodiments, according to the space size, the silver reflector's number and position can be set according to actual requirements. The optical distance of the pump light being equal to that of the probe light can be realized by reasonable design and layout.

The first light path module A subsequently comprises the second diaphragm 7, the first lens 8, the barium metaborate crystal 9, the silicon wafer 10, the first parabolic mirror 11, and the second parabolic mirror 12. The pump light is swerved by the silver reflectors 5, 6 to pass through the second diaphragm 7 to be further collimated. The pump light passes through the first lens 8 (the first lens 8 is a focusing lens). After being focused, the pump light (femtosecond pulse light) ionizes air to form a section of plasma filament and radiates a terahertz pulse by the barium metaborate crystal ($Ba(BO_2)_2$, BBO). In this embodiment, the barium metaborate crystal (BBO) 9 is placed straying from the focus of the first lens 8 to avoid the focused light being too bright, damaging the barium metaborate crystal (BBO) 9.

The barium metaborate crystal (BBO) 9 is a new ultraviolet doubled crystal with a broad optical transparency range (190 nm~3500 nm) and a phase matching range (409.6 nm~3500 nm), a large non-linear optical coefficient, a high photo damage resistance threshold, a broad temperature bandwidth and a good optical homogeneity. Because the titanium sapphire femtosecond laser 1 radiates a 800 nm femtosecond laser light pulse, which is used to generate a 400 nm frequency doubled light by the barium metaborate crystal. Meanwhile, a 800 nm fundamental frequency light is focused to ionize air to form plasma. The 400 nm frequency doubled light is applied on the plasma filament to drive plasma to radiate a terahertz pulse. Terahertz field is generated from focusing femtosecond pulse to excite gas ionization to form plasma filament radiation. There is no material's damage threshold, and high power laser light can be used to generate strong terahertz radiation. The terahertz radiation optimization can be realized by turning the angle of the barium metaborate crystal.

In other embodiments, the barium metaborate crystal (BBO) can also be other non-linear optical rectifying crystal, such as yttrium vanadate ($YVO_4$) or Calcite, or similar birefringent materials.

In other embodiments, the barium metaborate crystal 9 can be replaced by an active photoconductive antenna. The photoconductive antenna is composed of a substrate and two metal electrodes evaporating thereon. After applying a bias voltage between the two metal electrodes, when the excited light is the femtosecond laser light, the radiated electromagnetic wave is the terahertz radiation. Generally, low-temperature-grown gallium arsenide (LT-GaAs) photoconductive antenna is used.

The 800 nm fundamental frequency light and the 400 nm frequency doubled light are filtered from the terahertz pulse radiated by barium metaborate crystal ($Ba(BO_2)_2$, BBO) by the silicon wafer 10, only penetrating the terahertz pulse. Because the terahertz pulse is a cone radiation, the first parabolic mirror 11 and the second parabolic mirror 12 are placed behind the silicon wafer 10, and the first parabolic mirror 11 and the second parabolic mirror 12 are placed oppositely. The first parabolic mirror 11 is used to collimate the cone terahertz pulse and the second parabolic mirror 12 is used to focus the collimated parallel terahertz pulse.

The second light path module B subsequently comprises the delay line device 14, the chopper 15, the half wave plate 16, the Glan prism 17, the second lens 18, and the third diaphragm 19. The probe light passes through the delay line device 14 after being swerved by the silver reflector 13. The delay line device 14 comprises an optical delay line control device and an optical delay line. The information processing device 28 controls the movement of the optical delay line by the optical delay line control device. The delay line device 14 is used to detect the terahertz pulse node by node in space by the way of step scan to obtain the terahertz time-domain waveform. The probe light processed by the delay line device 14 passes through the chopper 15 to provide modulation frequency to the subsequent lock-in amplifier 27. Next, the probe light's polarization is adjusted after passing through the half wave plate 16 and the Glan prism 17 to be a linearly polarized light. The probe light with linear polarization, after being focused by the second lens 18 and collimated by the third diaphragm 19, is combined with the terahertz pulse focused by the second parabolic mirror 12 at the beam combiner 21. The beam combiner 21 is used to combine the generated terahertz pulse with the probe light and ensures that the optical distance of the pump light is equal to that of the probe light.

The combined light beam to be detected carrying terahertz pulse information is detected by the detection device C. The combined terahertz pulse and the linearly polarized probe light colinearly pass through the first electro-optical crystal 22. Due to the photoelectric effect, the terahertz pulse will modulate the refractive index of zinc telluride crystal to make it produce Pockels Effect. The probe light passing through the first electro-optical crystal 22 will be birefringent and be linearly polarized to be elliptical polarization. The refractive index after modulated will generate a phase delay to the components o light and e light of the probe light. Subsequently, the combined light passes through the second electro-optical crystal 23, wherein the first electro-optical crystal 22 and the second electro-optical crystal 23 have the same thickness and are seamlessly integrated together. After passing through the second electro-optical crystal 23, there is a phase compensation to the o light and the e light with phase delay. The phase delay of the two components o light and e light of the probe light can be reduced to minimum by adjusting the crystal axis angle of the first electro-optical crystal (zinc telluride crystal) 22 and the second electro-optical crystal (zinc telluride crystal) 23. Wherein both of the first electro-optical crystal 22 and the second electro-optical crystal 23 are sphalerite crystal. In this embodiment, both of the first electro-optical crystal 22 and the second electro-optical crystal 23 are (001) crystal axis oriented zinc telluride crystal. In other embodiments, the first electro-optical crystal 22 and the second electro-optical crystal 23 can also be similar types of sphalerite crystal.

In this embodiment, the crystal axis angle of the first electro-optical crystal (zinc telluride crystal) 22 and the second electro-optical crystal (zinc telluride crystal) 23 is 180° (π). Since these is a π angle between the two zinc telluride crystals, the o light and the e light will not be completely separated even if the field intensity of the terahertz pulse arrives at dozens of milliwatt per centimeter, so as to avoid the terahertz signal being saturated because of too high terahertz pulse field intensity. The linear detection of the terahertz pulse is realized by simultaneously adjusting the crystal axis angle of the first electro-optical crystal (zinc telluride crystal) 22 and the second electro-optical crystal (zinc telluride crystal) 23, so as to improve measurement accuracy.

After being modulated the two zinc telluride crystals, the light beam to be detected passes through the quarter wave plate 24 and the Wollaston prism 25 to spatially separate the o light and the e light perpendicular to the polarization direction. The spatially separated o light and e light are respectively received by two photoelectric probes (D1, D2) of the differential detector 26. The photoelectric signal conversion is implemented by the differential detector 26 to output a small signal. The output small signal is amplified and analog-to-digital converted by the lock-in amplifier in synchronization with the chopper. The information processing device receives and stores the discrete data of the terahertz signal processed by the lock-in amplifier and can implement fast Fourier transform, transforming time-domain signal into frequency-domain signal. Utilizing the above frequency-domain and time-domain terahertz signals, the terahertz time-domain spectroscopy can be derived reversely according to signal data processed by corresponding physical model or principle. Specifically, the amplitude of the terahertz time-domain light field is determined by the following formula:

$$E_{THz} = (n^2 \gamma_{41})^{-1} \sqrt{\left(\frac{2\pi n L}{\lambda} * \frac{3}{4}\right)^{-1} * \arcsin(\Delta I / I)}.$$

wherein n is the intrinsic refractive index when zinc telluride crystal is not subjected to terahertz field, $\gamma_{41}$ is the electro-optical tensor of the zinc telluride crystal, L is the thickness of a zinc telluride crystal, $\lambda$ is the wavelength of femtosecond laser source, $\Delta I$ is the light intensity difference of the o light and the e light detected by the photoelectric detector, and I is the sum of the o light and the e light detected by the photoelectric detector. The first-order approximation formula of the amplitude of the terahertz time-domain light field derived by a traditional detection device is as follow:

$$E_{THz} = \left(\frac{2\pi}{\lambda} n^3 \gamma_{41} L\right)^{-1} * \left(\frac{\Delta I}{I}\right).$$

Compared with the first-order approximation formula of the amplitude of the terahertz time-domain light field, the second-order approximation formula of the amplitude of the terahertz time-domain light field further improves the revivification accuracy and the detectable range of terahertz signal.

The technical features in the above embodiments can be combined arbitrarily. For simplicity, not all possible combinations of the technical features in the above embodiments are described. However, these combinations of the technical features should be within the scope recited in this specification, provided that there is no conflict in these combinations of the technical features.

The above embodiments merely express several implementing ways specifically and in detail. However, this cannot be constructed as a limit to the scope of this invention. It should be noted that, persons skilled in the art can make many variations and modifications without departing from the spirit of this invention, all of which belong to the scope of this invention. Therefore, the scope of the present application should be determined by the terms of the accompanying claims.

What is claimed is:

1. A terahertz time-domain spectroscopy system, comprising:
    a femtosecond laser that radiates femtosecond laser light;
    a first diaphragm that collimates the femtosecond laser light;
    a beam splitter that splits the femtosecond laser light into a pump light and a probe light;
    a first light path module;
    a second light path module,
    wherein the pump light generates a terahertz pulse by the first light path module; the probe light generates a linear polarization probe light having the same optical distance as that of the pump light by the second light path module,
    a beam combiner that combines the probe light and the terahertz pulse to produce a light beam to be detected carrying the terahertz pulse information;
    a detection device configured to detect the light beam to be detected, in the propagation direction of the light beam to be detected, the detection device comprises a first electro-optical crystal, a second electro-optical crystal, a quarter wave plate, a Wollaston prism, a photoelectric detector, a lock-in amplifier, and an information processing device, wherein the first electro-optical crystal and the second electro-optical crystal have a same thickness, and wherein respective crystal axis angles of the first electro-optical crystal and the second electro-optical crystal is adjustable.

2. The terahertz time-domain spectroscopy system of claim 1, wherein the first electro-optical crystal and the second electro-optical crystal are sphalerite crystal.

3. The terahertz time-domain spectroscopy system of claim 2, wherein the information processing device determines the amplitude of the terahertz pulse according to $$E_{THz} = (n^2 \gamma_{41})^{-1} \sqrt{\left(\frac{2\pi n L}{\lambda} * \frac{3}{4}\right)^{-1} * \arcsin(\Delta I / I)},$$

wherein n is the intrinsic refractive index when zinc telluride crystal is not subjected to terahertz field, $\gamma_{41}$ is the electro-optical tensor of the zinc telluride crystal, L is the thickness of the zinc telluride crystal, $\lambda$ is the central wavelength of the femtosecond laser light, $\Delta I$ is the light intensity difference of o light and e light of the probe light detected by the photoelectric detector, and I is the sum of o light and e light detected by the photoelectric detector.

4. The terahertz time-domain spectroscopy system of claim 1, wherein the respective crystal axis angles of the first electro-optical crystal and the second electro-optical crystal is 180°.

5. The terahertz time-domain spectroscopy system of claim 1, wherein in a propagation direction of the pump light, the first light path module comprises a plurality of reflectors, a second diaphragm, a first lens, a terahertz pulse emitting device, a first parabolic mirror, and a second parabolic mirror,
    the terahertz pulse emitting device configured to radiate a terahertz pulse,
    the first parabolic mirror disposed opposite the second parabolic mirror, and the first parabolic mirror configured to collimate the terahertz pulse and
    the second parabolic mirror configured to focus the terahertz pulse.

6. The terahertz time-domain spectroscopy system of claim 5, wherein the first light path module further comprises a silicon wafer to filter stray lights, permitting the terahertz pulse to pass through the silicon wafer placed between the terahertz emitting device and the first parabolic mirror.

7. The terahertz time-domain spectroscopy system of claim 5, wherein the terahertz emitting device comprises an active photoconductive antenna or a passive non-linear optical rectifying crystal.

8. The terahertz time-domain spectroscopy system of claim 7, wherein the passive non-linear optical rectifying crystal comprises barium metaborate crystal.

9. The terahertz time-domain spectroscopy system of claim 1, wherein in a propagation direction of the probe light, the second light path module subsequently comprises a delay line device, a chopper, a half wave plate, a Glan prism, a second lens, and a third diaphragm,
    the chopper configured to provide modulation frequency for the lock-in amplifier, and
    the half wave plate and the Glan prism configured to adjust the polarization of the probe light.

10. The terahertz time-domain spectroscopy system of claim 1, wherein the photoelectric detector comprises a differential photoelectric detector.

* * * * *